US006869000B2

(12) United States Patent
Bauer et al.

(10) Patent No.: US 6,869,000 B2
(45) Date of Patent: Mar. 22, 2005

(54) APPARATUS FOR CUTTING BODIES HAVING A NON-CIRCULAR CROSS SECTION

(75) Inventors: Peter Bauer, Basel (CH); Herbert Happe, Lippstadt (DE)

(73) Assignee: Synthes (U.S.A.), Paoli, PA (US)

( * ) Notice: Subject to any disclaimer, the term of this patent is extended or adjusted under 35 U.S.C. 154(b) by 17 days.

(21) Appl. No.: 08/659,046

(22) Filed: Jun. 3, 1996

(65) Prior Publication Data

US 2002/0043139 A1 Apr. 18, 2002

Related U.S. Application Data

(63) Continuation-in-part of application No. 08/508,255, filed on Jul. 27, 1995, now abandoned.

(30) Foreign Application Priority Data

Aug. 8, 1994 (CH) ................................................ 2457/94

(51) Int. Cl.$^7$ ............................ B26F 3/00; B26B 13/00; A61B 17/56
(52) U.S. Cl. .................... 225/102; 225/96.5; 30/240; 30/244; 83/199
(58) Field of Search ........................... 83/13, 199, 200; 225/102, 1, 2, 93, 94, 95, 96, 96.5, 97; 81/3.55, 119, 177.1, 120; 606/79, 83, 167, 174; 30/175, 177, 92, 173, 191, 192, 193, 194, 205, 240, 244, 252, 278, 279.2; 7/125, 132; 72/458, 459

(56) References Cited

U.S. PATENT DOCUMENTS

| | | | | |
|---|---|---|---|---|
| 150,789 A | * | 5/1874 | Pugsley ................... 30/244 X |
| 358,884 A | | 3/1887 | Roberts .................. 225/102 X |
| 365,473 A | | 6/1887 | Hinsdale ................. 225/102 X |
| 564,625 A | | 7/1896 | Kelsea ......................... 81/119 |
| 690,083 A | | 12/1901 | Stolpe ......................... 83/199 |
| 740,612 A | * | 10/1903 | Baartmans ................... 30/244 |
| 825,401 A | * | 7/1906 | Merckens .................... 81/120 |
| 913,013 A | | 2/1909 | Jensen ........................ 225/102 |
| 955,287 A | * | 4/1910 | Schofield .................. 30/193 X |
| 1,133,805 A | * | 3/1915 | Klein ....................... 30/244 X |
| 1,285,926 A | * | 11/1918 | Bussler .................... 81/120 X |
| 1,318,454 A | * | 10/1919 | Kleinkopf ............... 81/177.1 X |
| 1,366,063 A | | 1/1921 | Culhane, Jr. ............... 225/96 X |
| 1,471,422 A | * | 10/1923 | Shearer .................... 30/175 X |
| 1,861,207 A | | 5/1932 | Burns ......................... 81/119 |
| 2,421,414 A | | 6/1947 | Ernst ....................... 83/200 X |
| 2,502,582 A | * | 4/1950 | Murphy et al. ............... 30/194 |
| 2,539,294 A | * | 1/1951 | Barnes ......................... 30/252 |
| 2,603,999 A | * | 7/1952 | Boutte ....................... 81/177.1 |
| 2,638,985 A | | 5/1953 | Ross ....................... 83/199 X |
| 2,704,888 A | * | 3/1955 | DuBois ........................ 30/244 |
| 3,156,394 A | | 11/1964 | Alles et al. ............. 225/102 X |
| 3,701,295 A | * | 10/1972 | Mende ................... 81/177.1 X |
| 3,739,962 A | | 6/1973 | Boborykin et al. ......... 225/102 |
| 3,885,307 A | * | 5/1975 | Papalardo ............. 30/279.2 X |
| 3,958,732 A | | 5/1976 | Aoyama et al. ......... 225/102 X |
| 4,058,893 A | * | 11/1977 | Boyajian ..................... 30/92 X |
| 4,656,903 A | | 4/1987 | Peyre ........................... 83/199 |
| 4,887,447 A | | 12/1989 | Schweitzer ............... 83/200 X |
| 5,065,653 A | | 11/1991 | Werner ....................... 83/199 |
| 5,085,361 A | | 2/1992 | Wagner ...................... 225/102 |
| 5,562,006 A | | 10/1996 | Pelosi, Jr. et al. ............ 81/119 |

FOREIGN PATENT DOCUMENTS

| | | | |
|---|---|---|---|
| DE | 2 261 281 | 6/1974 | |
| DE | 43 08 319 | 6/1994 | |
| FR | 1567604 | 5/1969 | ............... 225/96.5 |
| GB | 20244 | * 10/1901 | ................. 30/177 |
| GB | 2057953 | 4/1981 | ................. 225/102 |
| JP | 60-191714 | 9/1985 | ..................... 83/13 |
| SU | 564108 | 7/1977 | ............... 225/96.5 |
| SU | 584987 | 12/1977 | ..................... 225/2 |

* cited by examiner

Primary Examiner—Clark F. Dexter
(74) Attorney, Agent, or Firm—Jones Day

(57) ABSTRACT

Bodies with non-circular cross-sections are cut using a tool, by applying a torsional cutting process.

34 Claims, 6 Drawing Sheets

APPARATUS FOR CUTTING BODIES HAVING A NON-CIRCULAR CROSS SECTION

This application is a continuation-in-part of our application Ser. No. 08/508,255 filed Jul. 27, 1995 abandoned.

FIELD OF THE INVENTION

The invention concerns a procedure for cutting bodies having a non-circular cross section; a tool for cutting such bodies; and the cut body so produced.

BACKGROUND OF THE INVENTION

For cutting osteosynthetic plates in surgery, a cutting procedure using a cutting tool such as a shears or a cutting pliers is primarily used. Such a tool is known, for example, from DE-C1 43 08 319. Considerable force must be applied to cut through the osteosynthetic plates. In particular, the force applied by cutting pliers such as that referred to is very great, and the cut edges of the bone plates are deformed, or end up with a seam.

The present invention is intended to provide a procedure and a tool for cutting osteosynthetic plates without excessive force while insuring a clean, non-deformed cut edge.

SUMMARY OF THE INVENTION

In accordance with the invention, the problem referred to is solved by cutting the plate or other body using torsion applied by means of a tool having an upper shearing part and a lower shearing part, each having a cutting edge in direct contact with one another and having means for rotating said parts about an axis coincidental with the axis of the body to be cut.

The bodies to be cut can have any non-circular cross section, e.g. a cylindrical or prismatic cross section. In the following description, the procedure will be set forth using osteosynthetic plates with an approximately rectangular cross section. However, it will he understood that the invention may be used with other cross sections. Preferably, plates to which the invention is applied will have transverse division lines or indentations along their longitudinal axes into which the cutting tool can be placed.

A tool according to the invention comprises upper and lower shearing elements, each having a cutting edge, the cutting edge of each shearing element directly touching the cutting edge of the other. The tool is closely applied to the longitudinal surfaces of the plate to be cut, and the plate is cut by turning the two shearing elements relative to one another.

The invention possesses a considerable advantage in that the bodies can be easily cut with markedly less applied force, and that no deformation takes place outside the cut location. In addition, the cutting procedure can be carried out in a short time with a very simple device.

BRIEF DESCRIPTION OF THE DRAWINGS

The invention will be further described in connection with the accompanying drawings in which.

DETAILED DESCRIPTION OF THE PREFERRED EMBODIMENTS

Figure 1A:
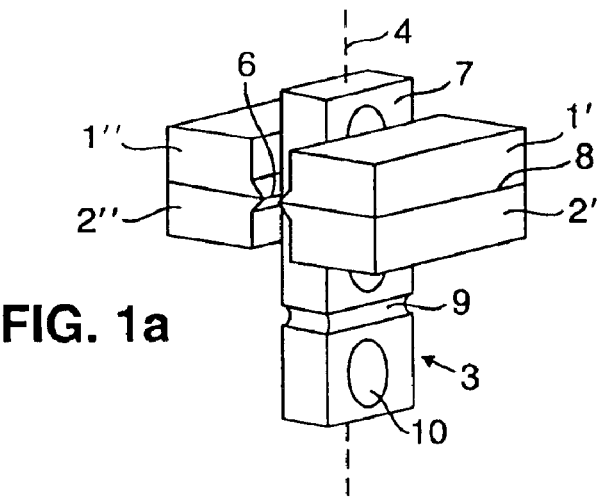
FIG. 1a is a perspective view of an osteosynthetic plate with a tool according to the invention schematically represented to illustrate the principle of the invention.
Figure 1B:
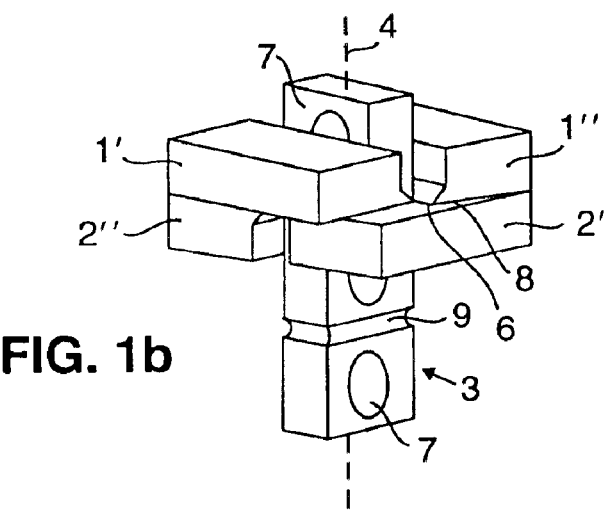
FIG. 1b is a schematic, perspective view showing the torsional motion of FIG. 1.
Figure 1C:
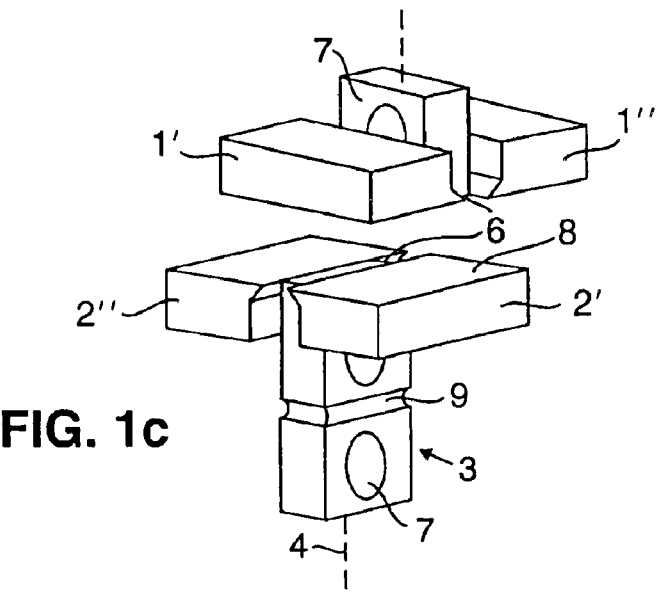
FIG. 1c is a schematic perspective view of the tool of FIGS. 1a and 1b, showing the osteosynthetic plate with its cut upper part lifted off.

In the schematic representation of FIGS. 1a–1c, each of the upper part 1 and the lower part 2 of a tool according to the invention is shown as two rectangular blocks 1', 1", 2' and 2". Each block 1', 1", 2', 2" is bevelled to form a sharp cutting edge 6. As shown in FIG. 1a, the cutting edges of the blocks in the upper part 1 touch directly the cutting edges of the lower part 2. These cutting edges are brought as closely as possible to the area 7 of the plate 3 to be cut. Preferably, the plate 3 has grooves or division lines 9 to which the cutting edges of the tool may be applied.

The plate 3 is shown as a bone plate useful in osteosynthesis, rectangular in cross section and having holes or recesses 10 for bone screws.

In accordance with the invention, to cut the plate 3, one (or both) of the blocks 1 and 2 are rotated relative to one another by more than 15° about the longitudinal axis 4 of the plate or other object to be cut, which is generally perpendicular to the plane of rotation 8 of the shearing device. This is illustrated in FIG. 1b where the upper block 1 has been rotated 90° relative to block 2 severing the upper part of plate 3. In FIG. 1c, the upper part is shown being detached from the remainder of the plate.

Figure 2A:
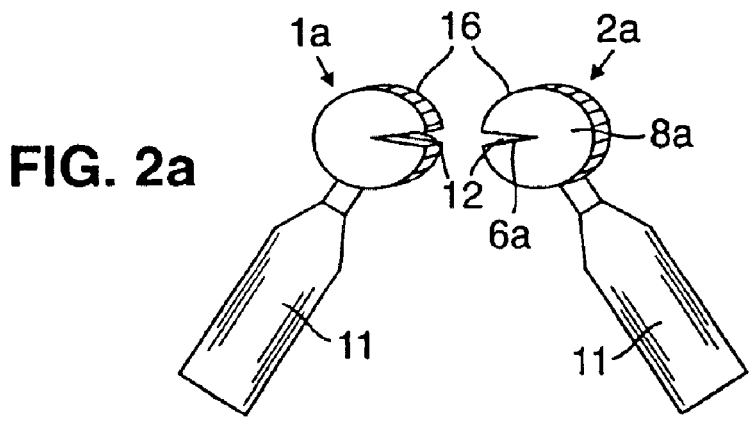
FIG. 2a is a schematic perspective view of an embodiment of the invention, including two round discs each having a slit and a lever arm.
Figure 2B:
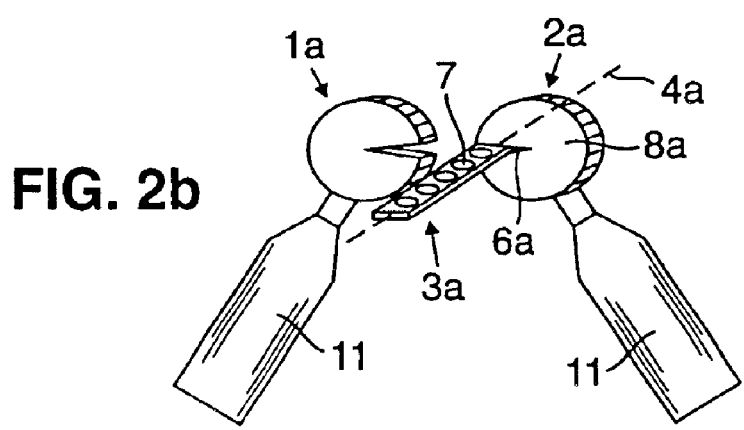
FIG. 2b is a schematic view of an osteosynthetic plate with the tool of FIG. 2a attached.
Figure 2C:
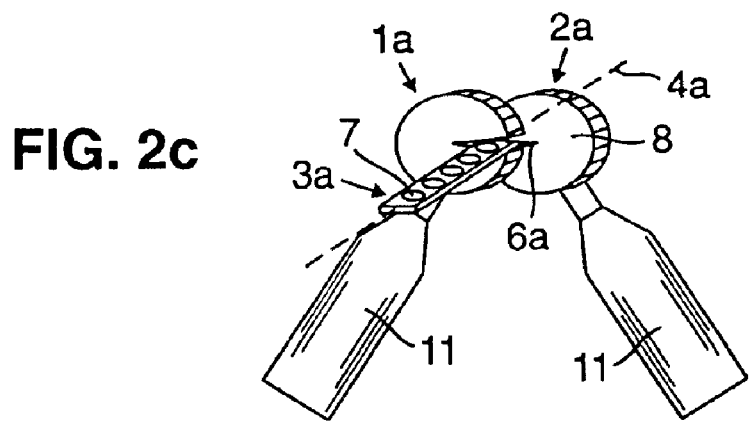
FIG. 2c is a schematic view of an osteosynthetic plate with the tool of FIG. 2a attached, illustrating the cutting procedure.

FIGS. 2a–2c show a specific form of the invention in which the shearing elements are circular discs. Referring to FIG. 2a, 1a and 2a depict the upper and lower shearing elements which have a disc-shaped form 16. The cutting edges 6a are formed by a slot 12 that tapers down or narrows in the direction of the center of the elements 1a and 2a. For exerting torsional force, lever arms 11 are attached to the elements 1a and 2a.

In FIG. 2b, plate 3a is inserted in slot 12 (which has a cutting edge 6a) of the lower shearing element 2a. The longitudinal axis 4a of the plate 3a again is approximately perpendicular to turning plane 8a.

In FIG. 2c, shearing elements 1a, 2a are positioned surface-to-surface with each other. Counterclockwise turning of the lever arm 11 of element 2a, with element 1a held fast or turned clockwise results in torsional cutting according to the invention.

Figure 3:
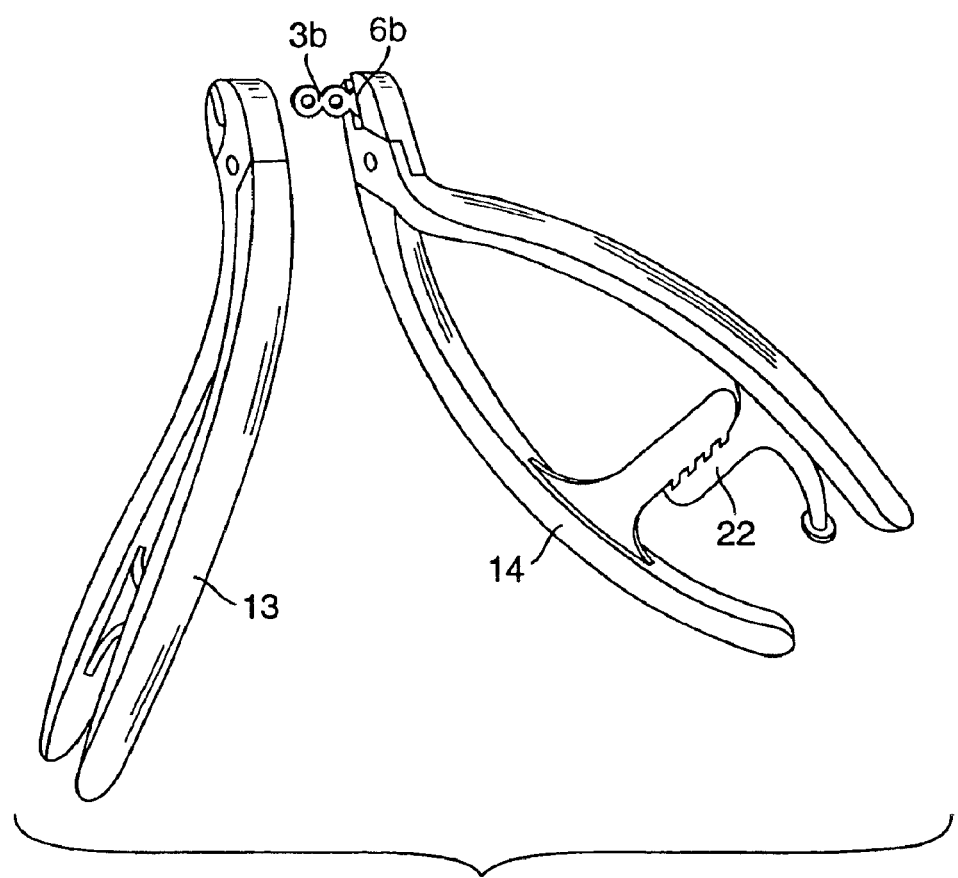
FIG. 3 is a schematic perspective view of another embodiment of the invention using two forceps.

In another embodiment of the invention, the cutting elements are the blades of two pair of cutting forceps. Referring to FIG. 3, the forceps 13, 14 grip with their cutting edges 6b into the dividing lines (not shown) of plate 3b, with the cutting edges 6b again to be brought into direct contact with each other on the longitudinal surfaces of plate 3b. Counterturning motion of the tensioned forceps 13, 14 leads to the desired torsion separation. A mechanical holding device 22 on the manual grip prevents the forceps from opening during the turning.

Figure 4:
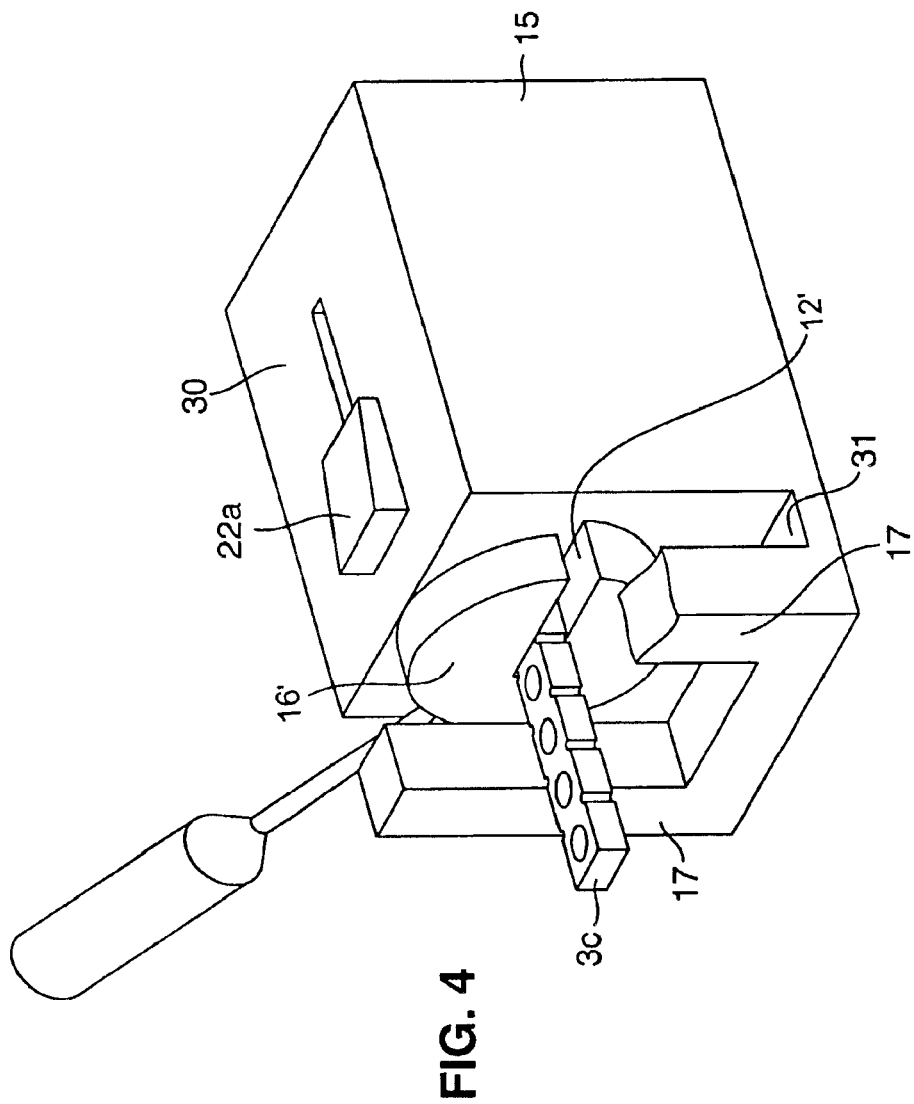
FIG. 4 is a schematic perspective view of a further embodiment of the invention including a tool with a holder and a disc with a cutting slot.
Figure 5:
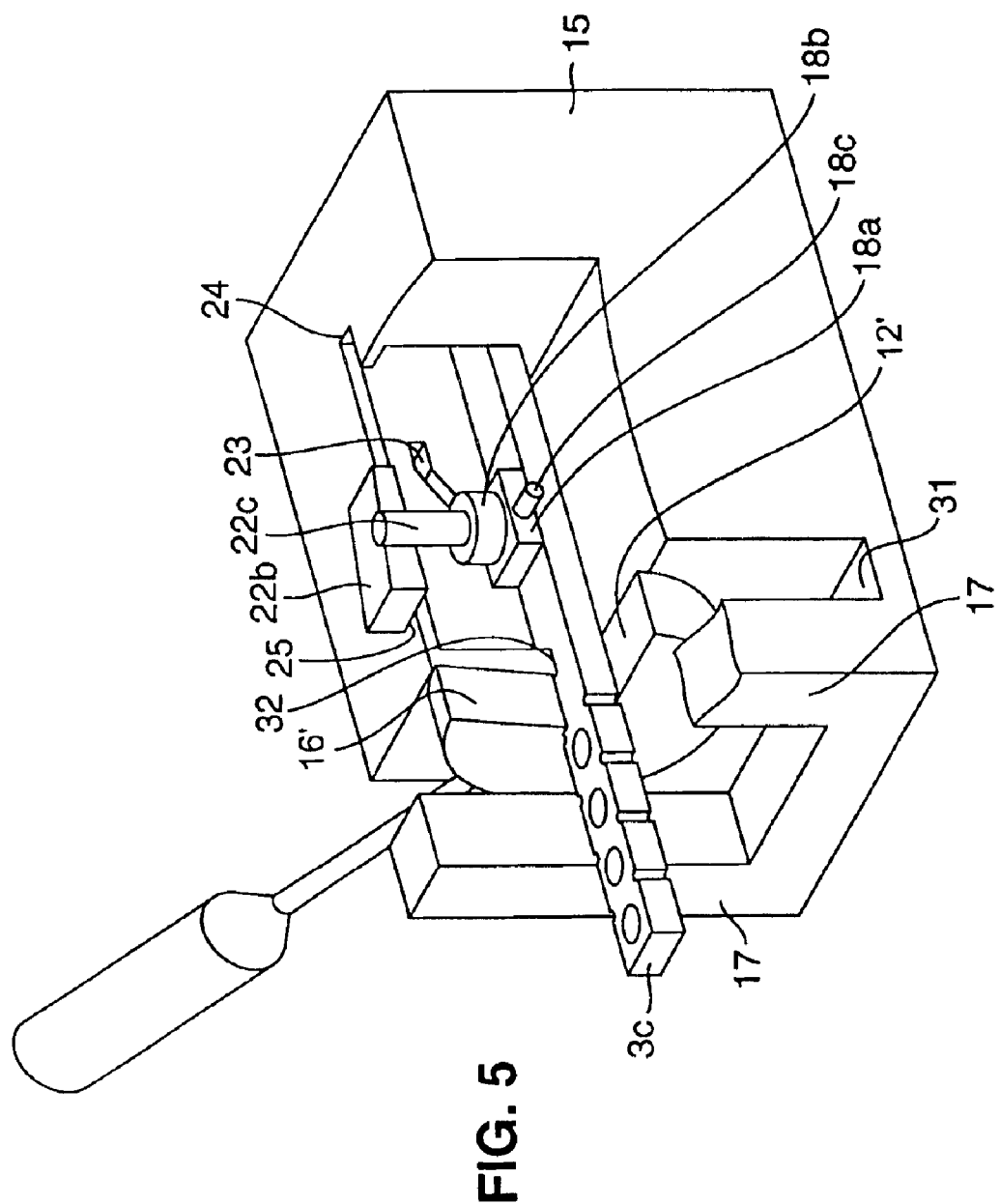
FIG. 5 is a schematic perspective view, partly broken away, of the tool of FIG. 4.

The tool shown in FIGS. 4 and 5 comprises a clamping mechanism 30 and a cutting unit 16' which is of the same general nature as that shown in FIGS. 2a–2c. As shown, the cutting unit 16' is inserted into a space 31 between a U-shaped entrance frame 17 and the casing 15 of clamping mechanism 30. As shown in FIGS. 4 and 5, a plate 3c to be cut is inserted through the U-shaped frame 17 through the aperture or slot 12' in cutting unit 16' and then into the clamping unit 30 through aperture 32.

The clamping mechanism according to FIGS. 4 and 5 includes a sliding assembly 22a and a clamping unit 18. The sliding assembly 22a comprises a slide 22b and an orthogonally oriented cylindrical rod 22c. The clamping unit 18 comprises a cylindrical sleeve 18b, a square clamp shoe 18a and bolts 18c. Bolts 18c, only one of which is shown, extend from each side of shoe 18a and ride in curved slots 23 in the interior wall of casing 15.

The sliding assembly 22a and clamping unit 18 are positively connected to each other. This is accomplished through a rod 22c which is telescopically seated in a sleeve 18b which in turn is attached to clamp shoe 18a. Rod 22c is seated in a socket in slide 22b and rides in a slot 24 in the upper surface of casing 15. When the sliding unit 22a has reached the right end of slot 24 the clamping unit 18 is forced to run up the curved slot 23 and releases the plate 3c. When the sliding unit 22a reaches the left end 25 of slot 24, the rod 22c is fully drawn out of shoe 18b and secures the plate 3c against longitudinal translation.

In FIG. 5 the clamping mechanism is shown in the closed state. If sliding assembly 22a is drawn backwards, clamping mechanism 18 runs up on the clamping curve 23 because it is positively connected to the sliding unit 22a. The rod 22c is then driven into the shoe 18b telescopically. A slight torsion cannot be prevented, but this is not deleterious for cutting quality because the true cut occurs at the edges of the plate insertion hole 25 and is performed by the plate cutting unit 16' and the thrust-bearing casing 15 which is placed on a flat surface.

Figure 6:
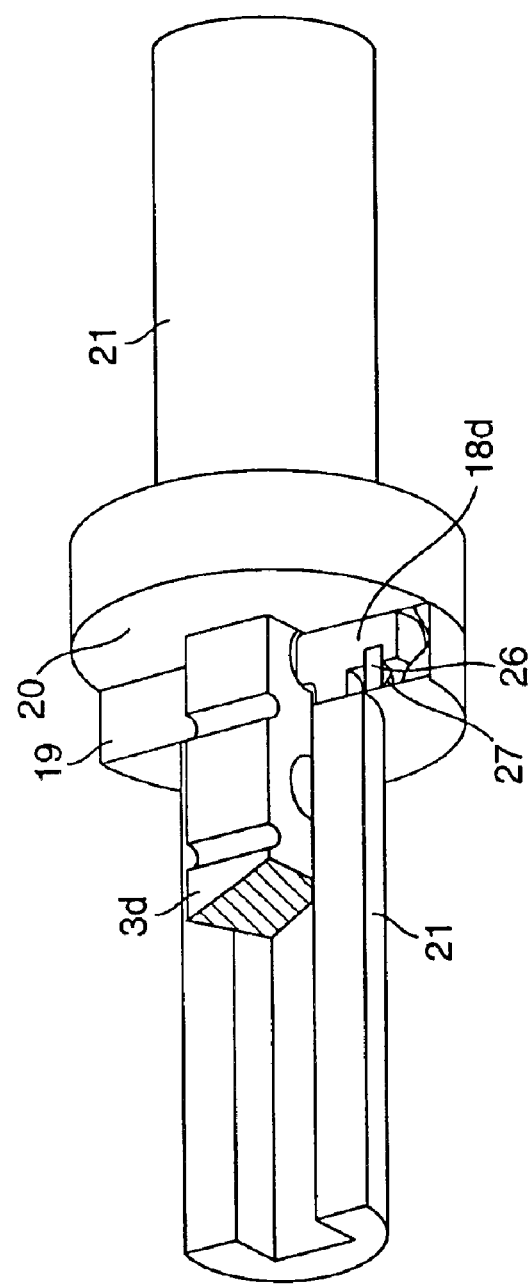
FIG. 6 is a schematic perspective view of yet a further embodiment of the invention having cylindrical shearing parts.

Still a further embodiment of the invention is shown in FIG. 6. Referring to FIG. 6, a first shearing element 19 and a second shearing element 20, are each provided with a manual grip 21. A plate 3d is clamped by closing a tension mechanism or clamping device 18d by turning motion of the first shearing element 19. This occurs because clamping shoe 18d is connected by means of a pin 26 with the front shearing element 19 which in turn is rotatively positioned on the handles 21. If element 19 is torsioned relative to handles 21, the pin 26 follows an eccentric curve 27 which is cut into the clamping shoe 18d and clamps the plate 3d after a certain relative torsion. The second shearing element 20 has a similar clamping device (not shown) and is positioned to adjoin the first shearing element 19. Likewise, by means of a turning motion, second shearing element 20 is clamped to the plate 3d. Then, by a counter torsional rotation of manual grips 21, plate 3 is separated.

During the turning motion, it would be advantageous to make provision, using a device configured in any manner (not shown in the drawings), so that the shearing elements would not be able to move away from each other. Also, use of such a device will allow the torque required for separating the body to be transmitted further via manual or mechanical drives to the shearing elements. In principle, it is possible that one or both shearing elements could be a component of such a device.

What is claimed is:

1. A bone plate cutting assembly for shearing by transverse forces a bone plate having a non-circular cross-section and a longitudinal axis, comprising:
   a first shearing element comprising
      a first handle for manipulation of the first shearing element; and
      a first head attached to the first handle and having a front face, a substantially flat back face, and an outer surface, the first head having a first slot through the front and back faces and extending from the outer surface towards an interior of the first head, the first slot extending across substantially one-half the back face and tapering from the outer surface toward the interior of the first head; and
   a second shearing element comprising
      a second handle for manipulation of the second shearing element; and
      a second head attached to the second handle and having a front face, a substantially flat back face, and an outer surface, the second head having a second slot through the front and back faces and extending from the outer surface towards an interior of the second head;
   wherein the first and second slots each define a set of opposing surfaces and at least one opposing surface of each set of opposing surfaces intersects the back face of the respective shearing element to form a bevelled cutting edge and wherein rotation of the first and second heads counter to one another about an axis of rotation with the heads directly touching each other at the cutting edges applies a torsional shearing force on the bone plate and the axis of rotation is selectively located within the first slot.

2. The assembly of claim 1, wherein each slot has a second cutting edge.

3. The assembly of claim 2, wherein each slot has opposing cutting edges.

4. The assembly of claim 2, wherein each handle has a longitudinal axis and the relative position of the longitudinal axes of the handles are configured at an acute angle when initiating rotation of the heads about the bone plate.

5. The assembly of claim 4, wherein the angle formed between the handles of each head decreases as the heads are rotated about the bone plate.

6. The assembly of claim 5, wherein the heads are disk shaped.

7. The assembly of claim 1, wherein the back faces are substantially smooth.

8. The assembly of claim 1, wherein at least a portion of each handle is tapered.

9. The assembly of claim 1, wherein the first and second heads are unconnected for selectively locating the axis and within rotation at of the two or more locations within the first slot.

10. The assembly of claim 9, wherein each opposing surface of each set of opposing surfaces intersects the back face of the respective shearing element to form a bevelled cutting edge.

11. The assembly of claim 1, wherein the axis of rotation is selectively located about half-way across the back face of the first slot.

12. The assembly of claim 1, wherein the heads are disk shaped.

13. The assembly of claim 1, wherein the back faces are substantially smooth.

14. The assembly of claim 1, each handle has a longitudinal axis and the relative position of the longitudinal axes of the handles are configured at an acute angle when initiating rotation of the heads about the bone plate.

15. The assembly of claim 14, wherein the angle formed between the handles of each head decreases as the heads are rotated about the bone plate.

16. The assembly of claim 15, wherein the heads are disk shaped.

17. The assembly of claim 1, wherein the second slot extends across substantially one-half the back face and tapers from the outer surface toward an interior of the first head.

18. The assembly of claim 17, wherein each opposing surface of each set of opposing surfaces intersects the back face of the respective shearing element to form a bevelled cutting edge.

19. The assembly of claim 1, wherein the first and second heads each are unitary members.

20. A bone plate cutting assembly for shearing by transverse forces a bone plate having a non-circular cross-section and a longitudinal axis, comprising:
    a first shearing element comprising
        a first handle for manipulation of the first shearing element; and
        a first disk shaped head attached to the first handle and having a front face, a back face, and an outer circumference, the first head having a first slot through the front and back faces and extending from the outer circumference towards an interior of the first head, the first slot extending across substantially one-half the back face; and
    a second shearing element comprising
        a second handle for manipulation of the second shearing element; and
        a second disk shaped head attached to the second handle and having a front face, a back face, and an outer circumference, the second head having a second slot through the front and back faces and extending from the circumference outer towards an interior of the second head;
    wherein the first and second slots each define a set of opposing surfaces and at least one opposing surface of each set of opposing surfaces intersects the back face of the respective shearing element to form a bevelled cutting edge;
    wherein the cutting edge formed in the first slot is non-parallel with respect to the other surface formed in the first slot so that the distance between the cutting edge formed in the first slot and the other opposing surface formed in the first slot decreases from the outer circumference toward the interior; and
    wherein rotation of the first and second heads counter to one another about an axis of rotation with the heads directly touching each other at the cutting edges applies a torsional shearing force on the bone plate and the axis of rotation is selectively located within the first slot.

21. The assembly of claim 20, wherein each slot has a second cutting edge.

22. The assembly of claim 21, wherein each slot has opposing cutting edges.

23. The assembly of claim 20, wherein the back faces are substantially smooth.

24. The assembly of claim 20, wherein at least a portion of each handle is tapered.

25. The assembly of claim 24, wherein each handle has a longitudinal axis and the relative position of the longitudinal axes of the handles are configured at an acute angle when initiating rotation of the heads about the bone plate.

26. The assembly of claim 25, wherein the angle formed between the handles of each head decreases as the heads are rotated about the bone plate.

27. The assembly of claim 20, wherein the axis of rotation is selectively located about half-way across the back face and within the first slot.

28. The assembly of claim 20, wherein the first and second heads are unconnected for selectively locating the axis of rotation at one of two or more locations within the first slot.

29. The assembly of claim 28, wherein each opposing surface of each set of opposing surfaces intersects the back face of the respective shearing element to form a bevelled cutting edge.

30. The assembly of claim 20, wherein each handle has a longitudinal axis and the relative position of the longitudinal axes of the handles are configured at an acute angle when initiating rotation of the heads about the bone plate.

31. The assembly of claim 30, wherein the angle formed between the handles of each head decreases as the heads are rotated about the bone plate.

32. The assembly of claim 20, wherein the second slot extends across substantially one-half the back face and the cutting edge formed in the second slot is non-parallel with respect to the other opposing surface formed in the second slot so that the distance between the cutting edge formed in the second slot and the other opposing surface formed in the second slot decreases from the outer circumference toward the interior.

33. The assembly of claim 32, wherein each opposing surface of each set of opposing surfaces intersects the back face of the respective shearing element to from a bevelled cutting edge.

34. The assembly of claim 20, wherein the first and second heads each are unitary members.

* * * * *